United States Patent [19]
Chu et al.

[11] Patent Number: 5,239,111
[45] Date of Patent: Aug. 24, 1993

[54] PROPYLENE GLYCOL MONOMETHYL ETHER PROPIONATE COMPOUND AND THE PROCESS FOR THE PREPARATION THEREOF

[75] Inventors: Tzong-Jeng Chu; Neng-Hui Chu; Peng-Fei Lee, all of Kaohsiung Shan, Taiwan

[73] Assignee: Shiny Chemical Industrial Co., Ltd., Kaohsiung, Taiwan

[21] Appl. No.: 960,736

[22] Filed: Oct. 14, 1992

[51] Int. Cl.$^5$ .............................................. C07C 67/10
[52] U.S. Cl. .................................................. 560/263
[58] Field of Search .................... 560/263, 240, 182

[56] References Cited

U.S. PATENT DOCUMENTS

| | | | |
|---|---|---|---|
| 4,298,758 | 11/1981 | Cook et al. | 560/263 X |
| 4,323,513 | 4/1982 | Dombek | 560/263 X |
| 4,476,332 | 10/1984 | Nalepa | 560/263 X |
| 4,544,453 | 10/1985 | Gupta | 560/263 X |
| 4,699,998 | 10/1987 | Green | 560/263 X |

Primary Examiner—Arthur C. Prescott
Attorney, Agent, or Firm—Pro-Techtor International

[57] ABSTRACT

A propylene glycol monomethyl ether propionate compound is obtained by the esterification of propylene glycol monomethyl ether with propionic acid at an elevated temperature above 80 °C. in the presence of acidic catalyst and azeotropic agent. This compound is rectified for removing acid residue and moisture in order to yield the desirable product having high purity.

6 Claims, 2 Drawing Sheets

PROPYLENE GLYCOL MONOMETHYL ETHER PROPIONATE COMPOUND AND THE PROCESS FOR THE PREPARATION THEREOF

FIELD OF THE INVENTION

This invention relates to propylene glycol monomethyl ether propionate having the formulas

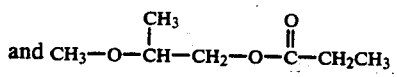

and $CH_3-O-CH(CH_3)-CH_2-O-C(=O)-CH_2CH_3$ obtained by the reaction between propylene glycol monomethyl ether and propionic acid.

BACKGROUND OF THE INVENTION

Organic ester compounds are good solvent widely used in synthetic resin industry, such as for paints, inks, adhesives and detergents. At present, ether compounds are mainly divided into two categories, i.e. E series and P series. The E series of ether compounds are obtained from the synthesis of alcohols and ethylene oxide while P series of ether compounds are obtained from the synthesis of alcohols and propylene oxide. The related ester compounds thereof are primarily acetate esters, whereas no propionate ester products have been developed so far. In recent years, it has been found that the E series of ethers or acetate ester compounds thereof when inhaled into human body are likely decomposed into alkoxy acetic acid ether and in turn induce the erythrocyte becoming abnormal and thus toxic to the genital organ. On the other hand, P series would not cause these damages. At present, propylene glycol monomethyl ether acetate of P series is inferior to the solubility against unsaturated polyesters or polyurethane resins as well as the drying capability of the coating thereof. Therefore, it is urgently demanded to develop a kind of solvent having not only excellent solubility and drying capability but also low toxicity.

Directing to this requirement, the inventors of the present application endeavored in positive research and development, and eventually produced successfully propylene glycol monoethyl ether propionate with best result.

SUMMARY OF THE INVENTION

An object of the present application is to provide a novel propylene glycol monomethyl ether propionate compound.

Another object is to provide a process for the preparation of propylene glycol monomethyl ether propionate (called "PMP" hereunder), which comprises reacting propylene glycol monomethyl ether (called "PMG" hereunder) obtained by synthesis reaction of methanol and propylene oxide under high pressure at high temperature, and propionic acid in the presence of acidic catalyst.

Further object is to the PMP as a solvent, especially in the fields of paints, inks, adhesives and detergents industries.

DETAILED DESCRIPTION OF THE PREFERRED EMBODIMENTS

Figure 1:
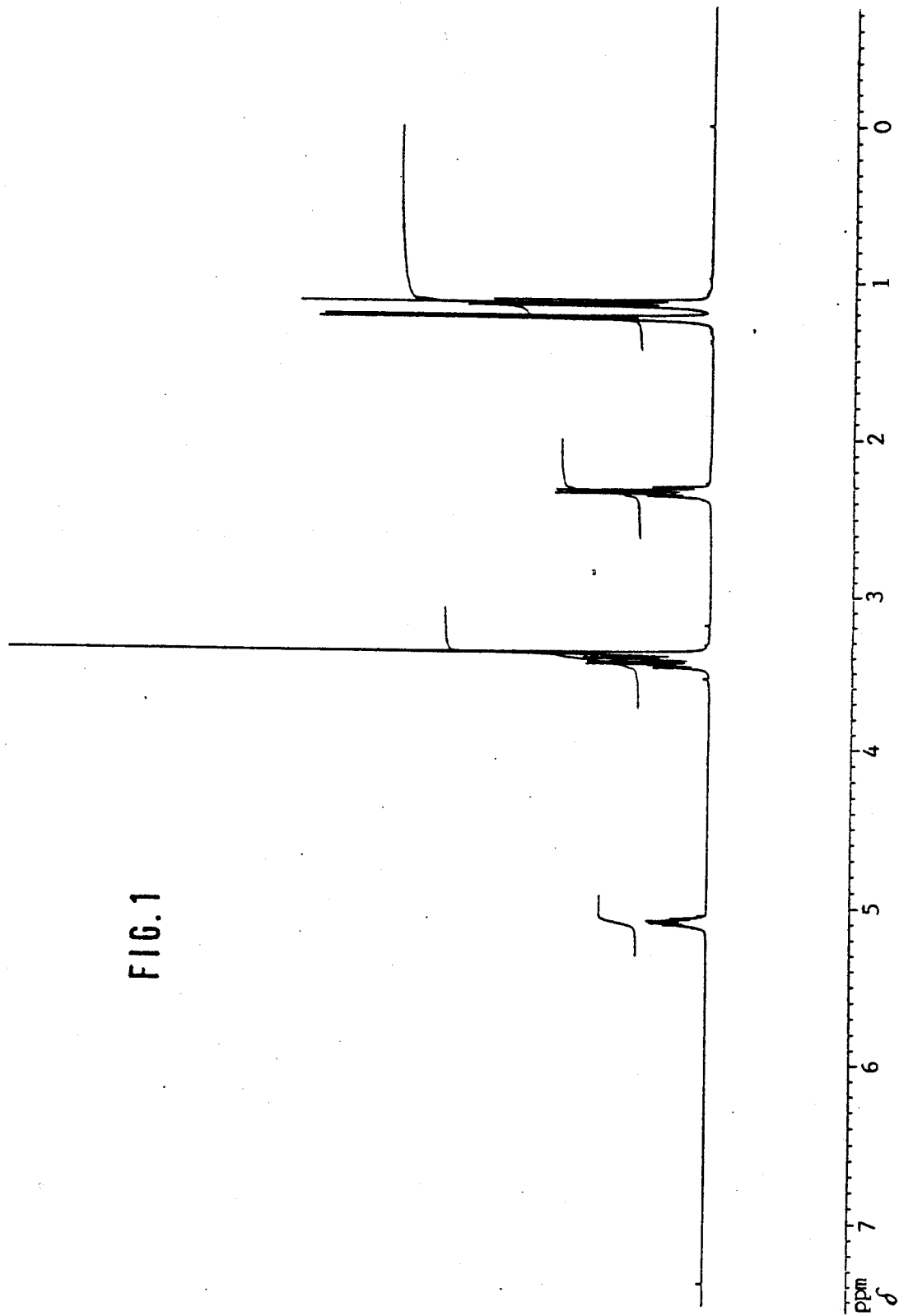
FIG. 1 shows a NMR'H spectrum of PMP produced according to the present invention.

The process for the preparation of PMP according to the present invention consists of batch and continuous processes. In general when the moisture generated during the reaction is not removed, the reaction system is likely reached an equilibrium state which would hinder the increase of productivity and thus disadvantageous to industrial production. Therefore, in the process of the present invention, no matter whether batch or continuous process is adopted, the reaction system may be added with aromatic compound as an azeotropic agent. The azeotropic component so added must be incompatible with water and has azeotropic effect with water. Aromatic compound is good in meeting these requirement.

In the batch process, the reactants and azeotropic solvent are placed into the reactor for carrying out the reaction at the azeotropic temperature while removing the water and recycling the azeotropic solvent. After the end of the reaction, the product and azeotropic solvent are separated by fractionating distillation so as to obtain the product of high purity.

In the continuous process, the starting materials are fed at a given flow rate on the end hand, and the water is withdrawn continuousely from the top of the fractionator during process of the reaction on the other hand. The azeotropic solvent is recycled while the reaction system containing the product PMP in a concentration of a certain extent presented in the reactor is transferred into a rectifying tower in order to proceed the fractionating distillation to remove a minor amount of unreacted ether, acid and PMP. Thereby, a product of high purity is obtained.

According to the process for the preparation of PMP in the present application, the starting materials of PGM and propionic acid are reacted at an elevated temperature above 80° C. in the presence of acidic catalyst and azeotropic agent for taking place the esterification to produce crude PMP. The product is then separated by rectification for removing the unreacted acid and generated water to obtain PMP of high purity.

For the starting material, the molar ratio of PGM to propionic acid is generally in the range of 0.6 to 3.0, preferably from 1.1 to 1.5, in which PGM is in excess with respect to propionic acid. If the molar ratio is smaller than 0.6 or greater than 3.0, after the reaction is accomplished, either party in the reaction system will leave unreacted residue in great excess so that not only more energy consumption will be rendered during the rectifying process, but also the rectifying time required is increased so as to decrease the production. If propionic acid is excess too much, namely the molar ratio smaller than 0.6, the reaction rate will be remarkably dropped. The reason is unclear but it is assumed that the acidic catalyst is subjected to buffering.

The catalysts used in the present invention include inorganic acids, such as sulfuric acid, hydrochloric acid and phosphoric acid, and organic acids, such as acetic acid, oxalic acid, citric acid, p-toluene sulfonic acid and methane sulfonic acid, among which the strong acids including sulfuric acid, p-toluene sulfonic acid or methane sulfonic acid is preferred. Propylene glycol monomethyl ether propionate obtained according to the present application has a boiling point of 160.5° C., while other reactants and products having respective boiling point of 120° C. for PGM, 140.8° C. for propionic acid and 100° C. for water. It is apparently easier to rectify this solution comparing the respective boiling point of 146° C. for propylene glycol monomethyl ether acetate, 118° C. for acetic acid and 120° C. for PGM as in the conventional case. This is one of the effects achieved by the process according to the present invention.

Another effect achieved is lower toxicity of PMP against the metabolic organs. In accordance with NOEL (NO Observable Effect Level) published by Environment Protection Agency of U.S.A., E and P series of esters for rabbit are 30 and 3000 ppm, respectively. PMP of this invention belongs to P series and thus has very low toxicity against to genital organ.

Further, PMP has better solubility to various resins. For example, propylene glycol monomethyl ether acetate has final solvent percentages of 70% to alkyd resin while present PMP is over 90%, an excellent solvent is herewith proved.

In the process of the present invention, when the reaction is completed the reaction system must be treated by double rectification. Primary rectification is a dehydration and deacidification procedures. For enhancing the efficiency and saving the energy, an azeotropic agent selected from aromatic organic solvent comprising benzene, toluene, xylene and cyclohexane is added in amount of 6 to 30% with respect to combined starting materials in order to reduce the azeotropic temperature in rectification. At secondary rectification, only two components of tether and ester are left, which are likely completely fractionally distilled based on the difference of boiling points between two components, thereby a product of high purity is obtained.

Now, the present invention will be further described by means of the following Examples which are merely for the purpose of illustration and by no means of any limitation therefor.

EXAMPLE 1

Into the reator having a volume of 3 liters, 1172 ml of PGM and 746 ml of propionic acid were introduced. After mixing 200 ml of xylene and 10 grams of p-toluene sulfonic acid were added. Then the temperature was brought to reflux temperature at 142° C. to carry out the reaction for 5 hours. During this period the dehydration was taken place simultaneously in favor of the progression of the reaction. The reaction solution was analyzed by gas chromatography and found the following composition:

| | |
|---|---|
| PMP | 69.91% |
| PGM | 15.34% |
| propionic acid | 6.33% |
| xylene | 7.78% |
| water | 0.59% |

This solution was further treated by double rectification, PMP compound having a purity greater than 99.9% was obtained.

Figure 2:
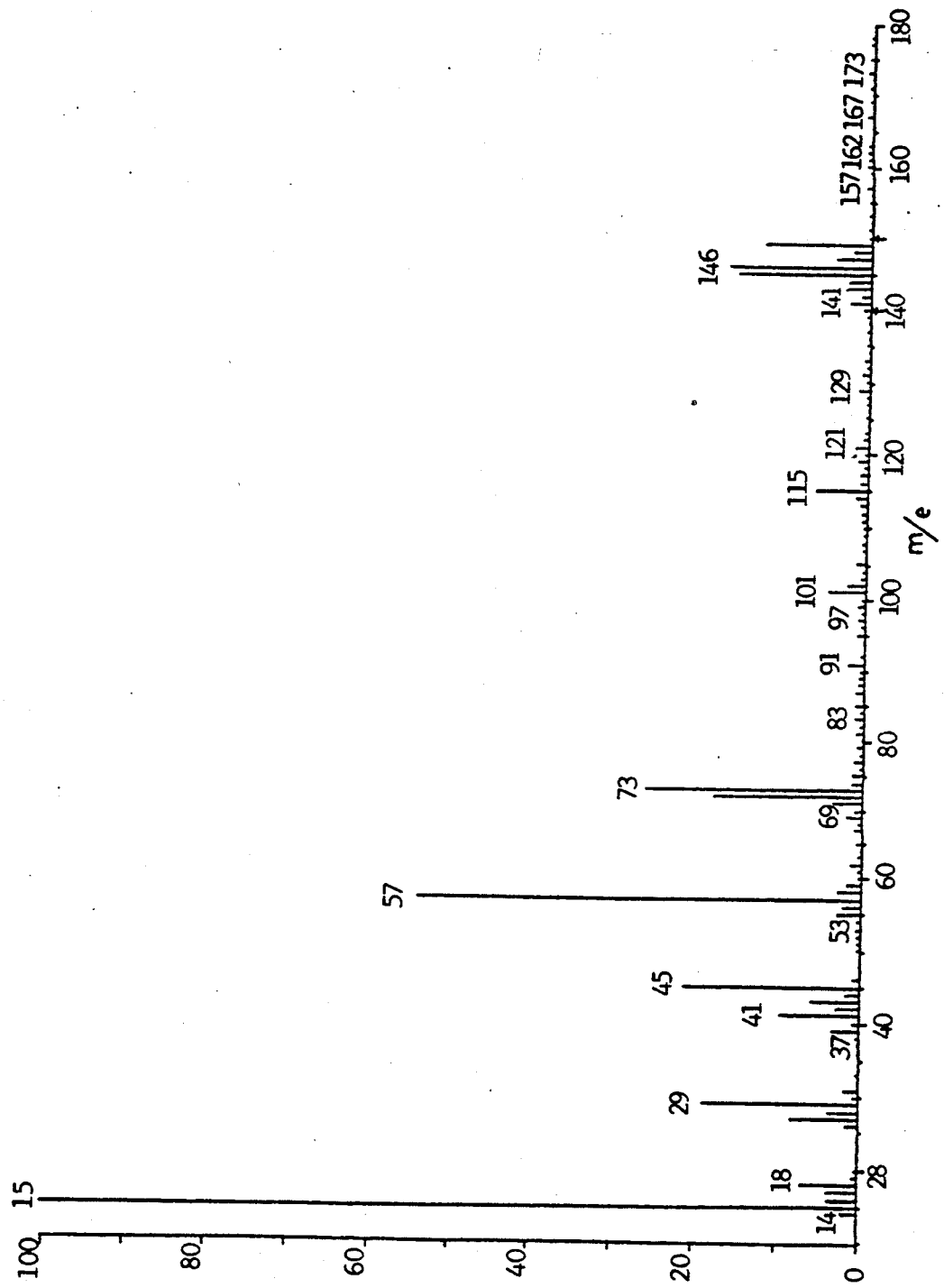
FIG. 2 shows a mass spectrum of PMP produced according to the present invention.

This PMP compound was characterized by NMR'H spectrum as shown in FIG. 1 and mass spectrogram as shown in FIG. 2, thereby the chemical structure thereof can be determined as

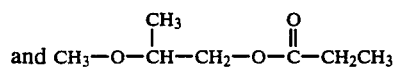
and $CH_3-O-CH(CH_3)-CH_2-O-C(=O)-CH_2CH_3$

EXAMPLE 2

Into the reactor having a volume of 3 liters, 1172 ml of PGM and 746 ml of propionic acid were introduced. After mixing 10 grams of P-toluene sulfonic acid were added. Then the temperature was brought to 99.1° C. the azeotropic temperature of water and propionic acid, to carry out the reflux reaction for 5 hours. Since no azeotropic solvent was added, the aqueous layer was impossibly separated, therefore the equilibrium was likely reached. This reaction solution was analyzed by gas chromatography and found the following composition:

| | |
|---|---|
| PMP | 44.6% |
| PGM | 27.6% |
| propionic acid | 22.4% |
| water | 5.4% |

COMPARATIVE EXAMPLE

Into the reactor having a volume of 3 liters, 1172 ml of PGM and 572 ml of acetic acid were introduced. After mixing, 10 grams of P-toluene sulfonic acid were added. Then the temperature was brought to the reflux temperature of 97.5° C. to carry out the reaction for 5 hours. The reaction solution was analyzed by gas chromatography and found the following composition:

| | |
|---|---|
| propylene glycol monomethyl ether acetate | 44.0% |
| acetic acid | 20.1% |
| PGM | 29.7% |
| water | 5.8% |

This solution was treated by double rectification, propylene glycol monomethyl ether acetate having a purity of 99% was obtained. The yield is too low to meet the inductrial requirement.

What I claim is:

1. Propylene glycol monomethyl ether propionate compound obtained by the reaction between propylene glycol monomethyl ether and propionic acid.

2. A process for the preparation of propylene glycol monomethyl ether propionate, comprising the steps of reacting propylene glycol monomethyl ether and propionic acid at elevated temperature above 80° C. in the presence of acidic catalyst and azeotropic agent for taking place the esterification to produce crude propylene glycol monomethyl ether propionate and removing the unreacted acid and water by rectification to obtain desirable propylene glycol monomethyl ether propionate having high purity.

3. The process as set forth in claim 2, wherein the molar ratio between propylene glycol monomethyl ether and propionic acid is in the range from 0.6 to 3.0.

4. The process as set forth in claim 2, wherein said catalyst is selected from a group consisting of sulfuric acid, P-toluene sulfonic acid and methane sulfonic acid.

5. The process as set forth in claim 2, wherein said azeotropic agent is selected from a group consisting of benzene, toluene, xylene and cyclohexane, in an amount of 6% to 30% by volume with respect to the sum of propylene glycol monomethyl ether and propionic acid.

6. Use of propylene glycol monomethyl ether propionate as the solvent for paints, inks, adhesives and detergents.

* * * * *